United States Patent [19]
Boldt

[11] 4,168,466
[45] Sep. 18, 1979

[54] MOISTURE TESTER

[75] Inventor: Robert R. Boldt, Taylor Ridge, Ill.

[73] Assignee: Agridustrial Electronics, Inc., Bettendorf, Iowa

[21] Appl. No.: 844,218

[22] Filed: Oct. 21, 1977

[51] Int. Cl.² ............................................. G01R 27/02
[52] U.S. Cl. .................................. 324/61 R; 324/61 P
[58] Field of Search ............................ 324/61 R, 61 P

[56] References Cited

U.S. PATENT DOCUMENTS

| | | | |
|---|---|---|---|
| 2,665,409 | 1/1954 | Rogers | 324/61 R |
| 2,726,366 | 12/1955 | Rogers | 324/61 P |
| 2,788,487 | 4/1957 | Grogg, Jr. | 324/61 R |
| 3,028,549 | 4/1962 | Stein | 324/61 R |
| 3,269,180 | 8/1966 | Schreiber | 324/61 P |
| 3,760,267 | 9/1973 | Williams | 324/61 R |
| 3,778,707 | 12/1973 | Vogel | 324/61 R |

FOREIGN PATENT DOCUMENTS 909021  9/1972  Canada ................................. 324/61 R

*Primary Examiner*—Stanley T. Krawczewicz
*Attorney, Agent, or Firm*—Trexler, Wolters, Bushnell & Fosse, Ltd.

[57] ABSTRACT

A continuous flow moisture tester includes first and second electrodes defining a capacitive-type test cell. The first electrode comprises a generally cylindrical tube of electrically conductive material, and the second electrode comprises a generally planar body of electrically conductive material disposed adjacent an inner wall of said first electrode member to define a substantially unobstructed passageway between the electrode members. Material carrying members are connected at an inlet and outlet of the passageway for providing a substantially constant flow of material therethrough and for maintaining the passageway substantially evenly filled with flowing material. An electrical circuit is connected with the test cell for producing a signal corresponding to the moisture content of the material flowing therethrough. The circuit is arranged for producing the above-described signal substantially independent of the density of the material or any variations therein, and in accordance with the electrical properties of the material-filled capacitive test cell.

8 Claims, 9 Drawing Figures

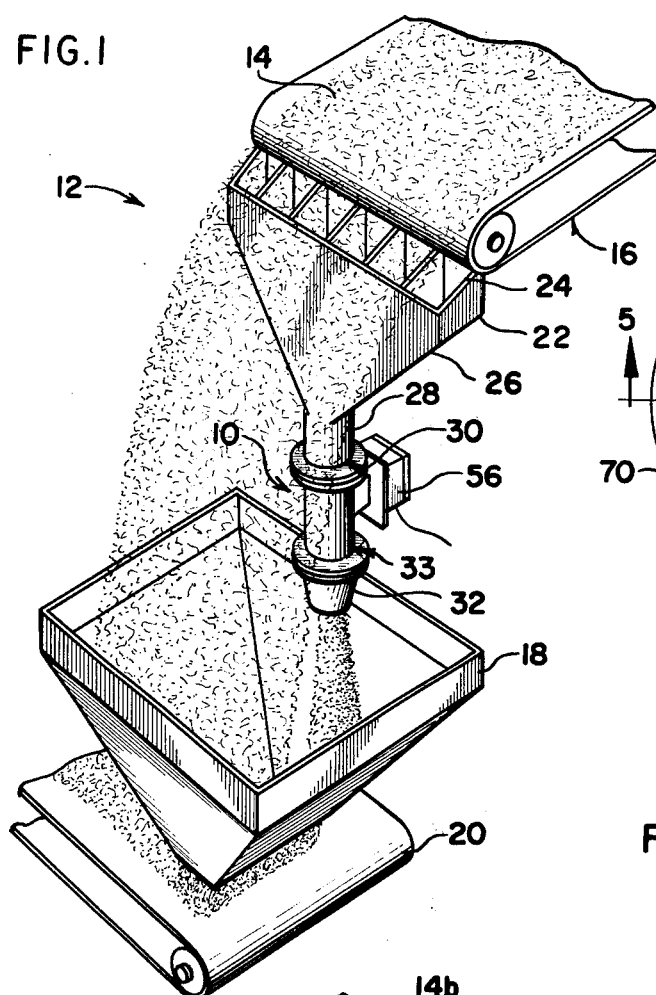
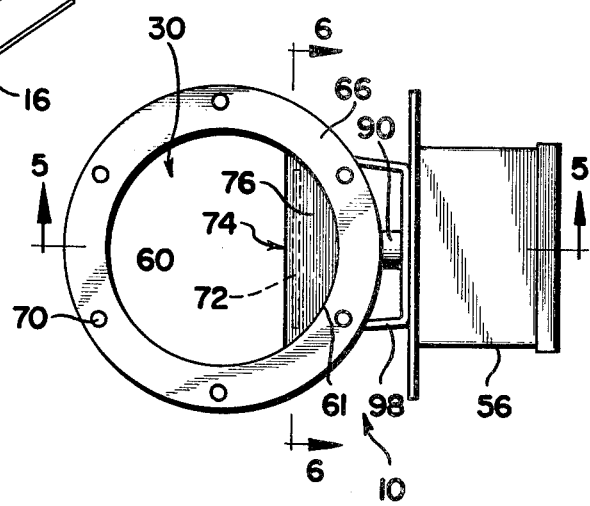
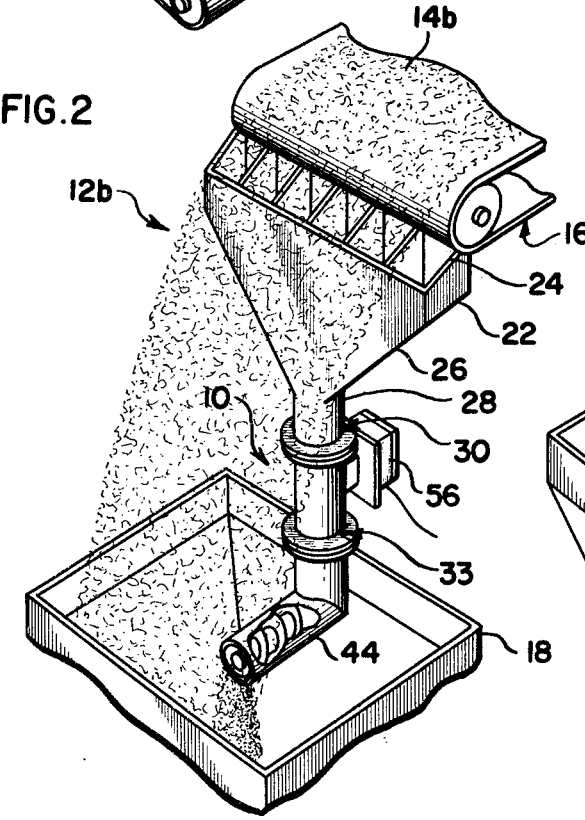
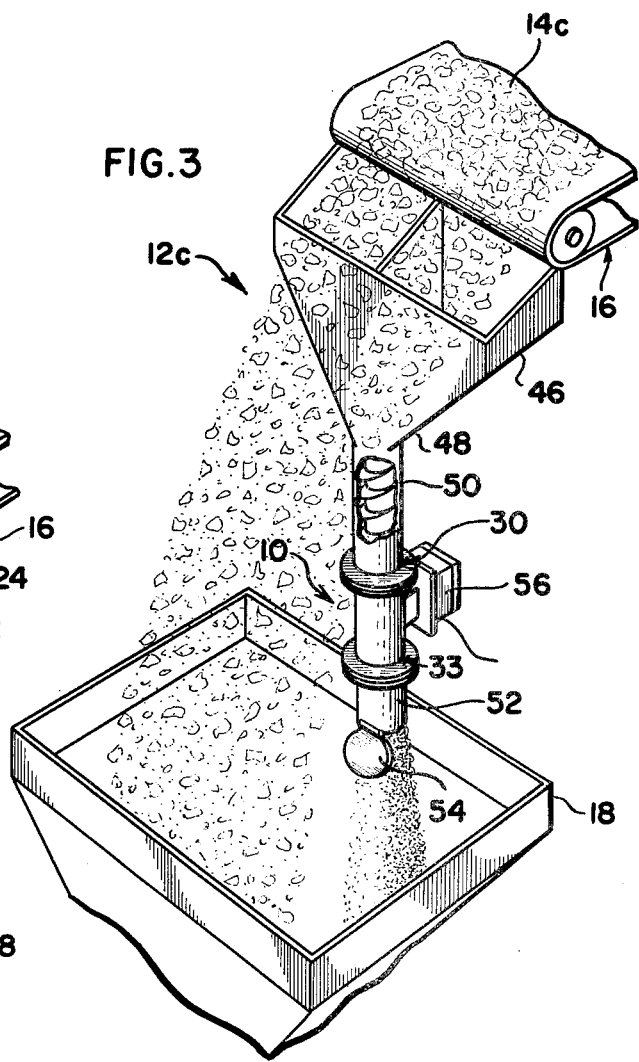

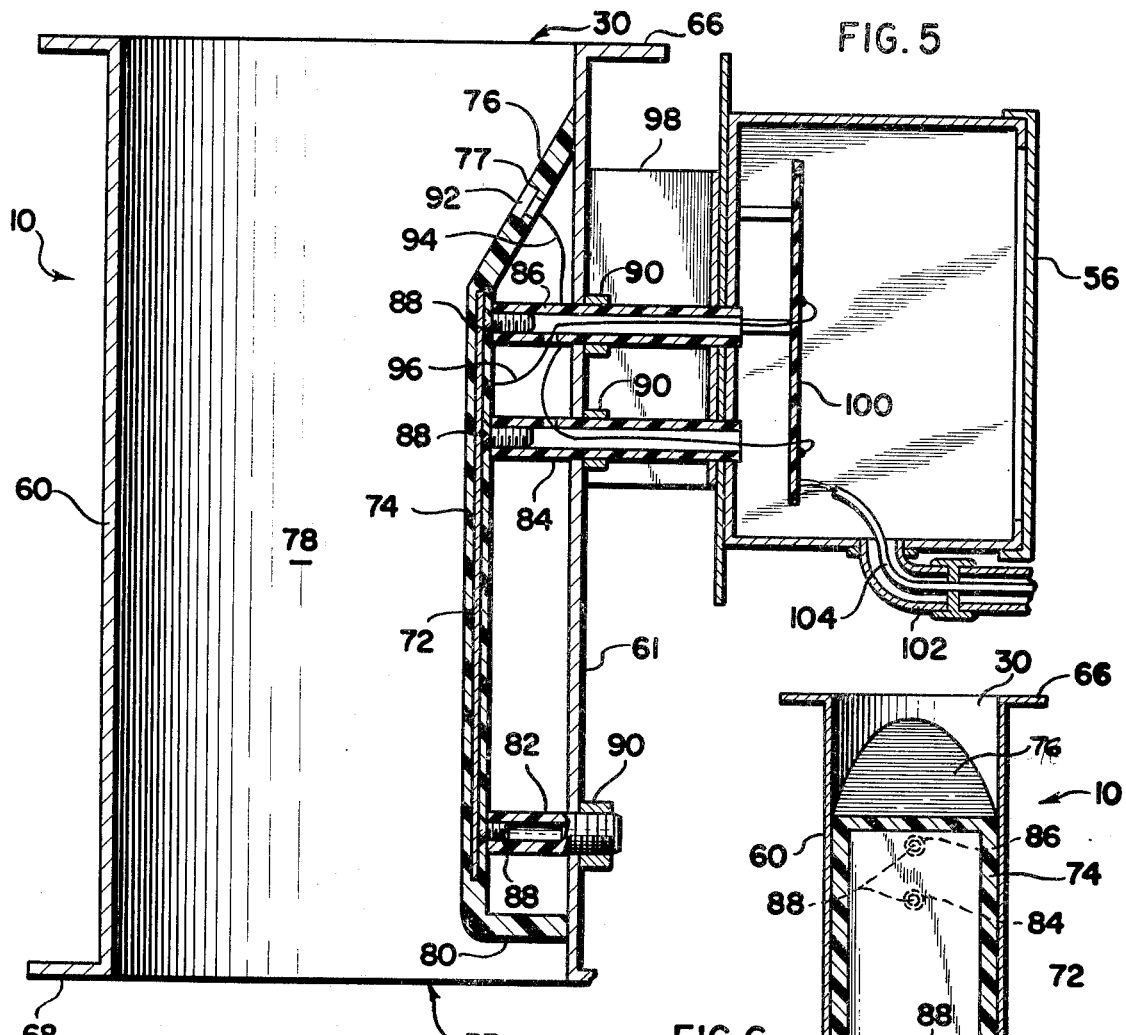
FIG. 5
FIG. 6
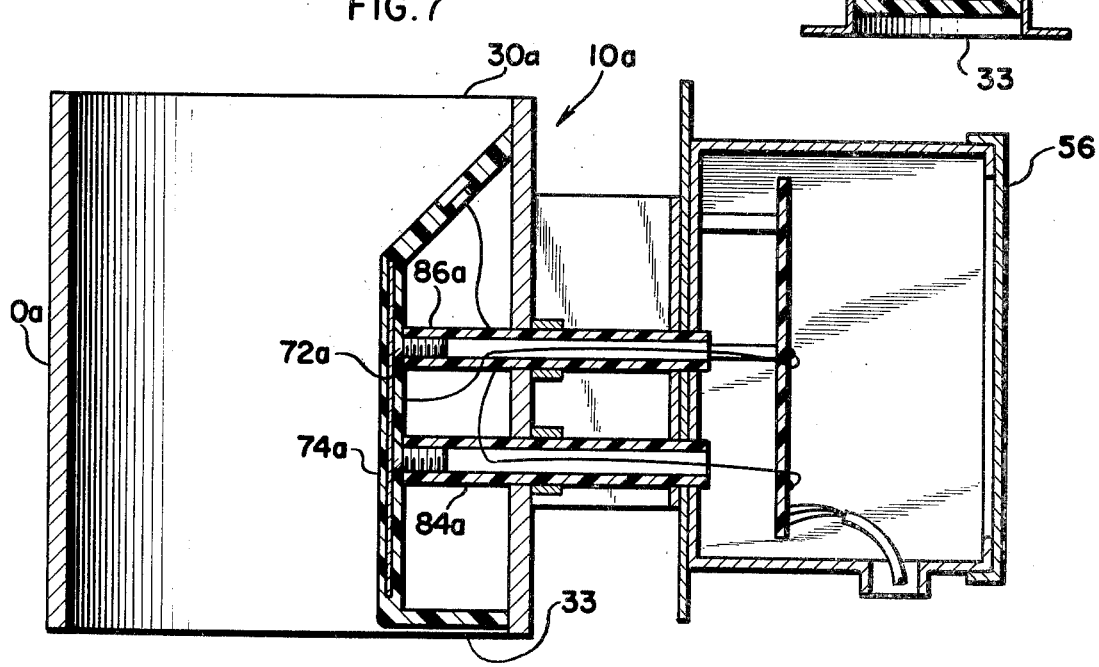
FIG. 7

MOISTURE TESTER

BACKGROUND OF THE INVENTION

This invention relates generally to test apparatus for determining the properties of materials, and more particularly to a continuous-flow moisture tester for measuring the moisture content of materials such as agricultural products being conveyed therethrough.

In the past moisture testers of the continuous flow variety have been adapted for measuring moisture content of granular material such as agricultural grains. Such moisture testers have included, for example, a test cell comprising a pair of parallel plates that function as a capacitor, the material to be tested being discharged from a chute and falling by gravity between the plates. Another prior art tester utilizes a test cell having cylindrical, coaxial electrodes, an enclosed top, an open bottom and upper side-wall exit apertures. This tester also includes a conveyor screw for forcing material to be tested upwardly through the open bottom of the test cell. A further prior art tester utilizes an open-ended test cell having inner and outer coaxial, cylindrical electrodes that have their axis vertical during use. In the latter coaxial electrode arrangement, it is necessary to provide a plurality of supporting cross rod members to support and hold the inner electrode coaxially within the outer electrode.

A common problem encountered in the foregoing arrangements is that of maintaining a substantially even and constant flow of material through the test cell, while keeping the cell substantially evenly filled with material to be tested. For example, it will be appreciated that the parallel plate arrangement presents a geometry difficult to keep evenly filled with flowing material. Moreover, when agricultural grains such as wheat, corn or the like are being tested, the side-wall exit apertures and the cross rods in the respective described coaxial electrode arrangements tend to collect foreign materials such as husks, stalks and the like, thereby causing voids in the grain flow and subsequent inaccuracies in moisture measurements taken therefrom. Further, plugging up of the test cell and loss of flow therethrough often occurs in both prior art arrangements. Additionally, certain of the foregoing types of moisture testers, while useful and generally quite successful when used with readily flowing materials such as wheat or corn, exhibit further aggravation of the above-noted problems when less readily flowing materials are sought to be tested thereby. For example, in the case of relatively low density, fine ground materials such as hominy feed, fish meal, cotton seed meal, prepelletized formula feed and the like, the material tends to bridge over and obstruct any restricted areas. Such areas may be in the cell, or in attached outlet devices, such as restrictor cones, commonly used with such moisture testers. Further, in the testing of bulkier fibrous materials such as chopped alfalfa, bermuda grass or the like, the foregoing problems become even more acute.

A related problem encountered in the foregoing types of prior art moisture testers is obtaining a reliable continuous moisture measurement of materials flowing therethrough, substantially unaffected by the difference in densities of different materials to be tested, as well as by variations in the density of a given material being tested. The prior art devices rely primarily upon various physical arrangements for attempting to maintain material at a constant predetermined density as it flows through the test cell. It will be apparent, however, that such arrangements may have problems in view of the plugging and voiding discussed above, and in view of the natural variations in density within a given batch of material being tested.

OBJECTS AND SUMMARY OF THE INVENTION

Accordingly, it is a general object of the present invention to provide an improved moisture tester which overcomes the limitations of the prior art by providing for a substantially unimpeded passageway through a capacitive type cell element thereof.

A more specific object of the present invention is to provide an improved moisture tester, in accordance with the foregoing object, further adapted to reliably obtain moisture measurements of a considerable variety of materials substantially independent of the densities thereof, as well as of the variations in density in a given batch of material being tested.

Another object of this invention is to provide a moisture tester, in accordance with the foregoing objects, further adapted to provide a substantially constant and even flow of material through the test cell while maintaining the cell substantially evenly filled with the flowing material.

Briefly, a moisture tester according to this invention comprises a first electrode member comprising, in a preferred embodiment, a generally cylindrical tube of electrically conductive material. A second electrode member comprises, in a preferred embodiment, a generally planar body of electrically conductive material disposed inside of said first electrode member closely adjacent an inner wall thereof, to define a substantially unobstructed passageway between the electrodes. The first and second electrode members are electrically isolated from each other to define therebetween a capacitive test cell. Material supply means is connected with the passageway for providing a substantially even and constant flow of material therethrough while cooperating with the passageway to maintain the passageway substantially evenly filled with flowing material. Circuit means are connected with the test cell for producing signal means corresponding to the moisture content of the material flowing therethrough in accordance with the electrical properties of said material-filled capacitive test cell, substantially independent of the density of the material being tested as well as any variations in said density.

Other objects, features and advantages of the invention will become apparent upon consideration of the following detailed description, together with the attached drawings, wherein like reference numerals are used throughout to designate like elements and components.

BRIEF DESCRIPTION OF THE DRAWINGS

FIG. 1 is a top perspective view of a moisture tester according to this invention mounted in conjunction with a belt conveyor;

FIG. 2 is a top perspective view of yet another embodiment of a moisture tester according to the present invention mounted in conjunction with a belt conveyor;

FIG. 3 is a top perspective view of still another embodiment of a moisture according to this invention mounted in conjunction with a belt conveyor;

FIG. 4 is a top view of a test cell according to this invention;

FIG. 5 is an enlarged sectional view of the test cell of FIG. 4, taken generally along the line 5—5 thereof;

FIG. 6 is a sectional view of the test cell of FIG. 4 taken generally along the line 6—6 thereof;

FIG. 7 is an enlarged sectional view, similar to FIG. 5 of a second embodiment of a test cell according to this invention

DETAILED DESCRIPTION OF THE ILLUSTRATED EMBODIMENTS

Figure 8A:
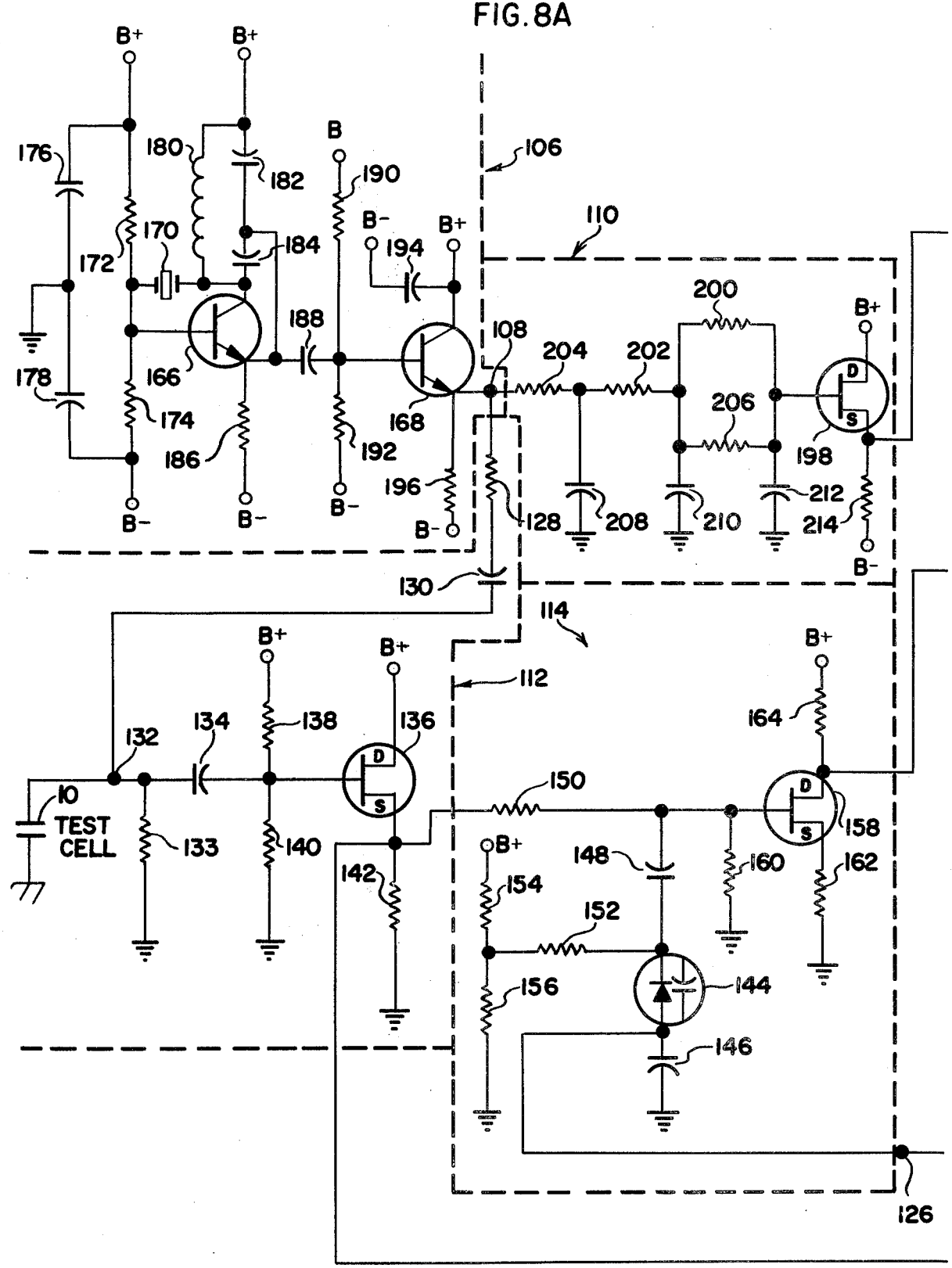
FIGS. 8A and 8B are schematic circuit diagrams of a moisture tester circuit in accordance with this invention.

Referring now in detail to the drawings, and in particular to FIGS. 1 through 4, a test cell designated generally 10 is advantageously adapted for use in measuring the moisture content of a considerable variety of materials.

With specific reference to FIG. 1, an embodiment of a moisture tester 12 in accordance with the present invention is illustrated, which embodiment is most beneficial for moisture measurement of readily flowing granular materials such as wheat, shelled corn and similar agricultural products. The moisture tester 12 includes the test cell 10, which is positioned in a generally upright or vertical orientation to receive material 14. The test cell 10 is constructed in accordance with features of the present invention, which will be more fully described hereinbelow. Material 14 to be tested is carried on a conveyor belt 16 to a hopper or chute 18 and delivered therethrough to be carried on a second conveyor belt 20. The conveyor belts 16 and 20 and hopper or chute 18 form no part of the present invention, and are included to illustrate a typical arrangement for conveying such materials. In accordance with a feature of the invention a material carrying member comprising a sampling chute or diverter 22 is provided closely adjacent an end of the belt 16, whereby most of the material flows over the sampling chute or deverter 22, while a portion is diverted therethrough to be delivered to the test cell 10.

In the embodiment of FIG. 1, the sampling chute 22 has an elongated, rectangular top intake portion 24 substantially coextensive with the width of the belt 16 and converging sides 26 joining the intake 24 with a circular outlet 28 coupled to a generally concentric circular inlet port 30 of the test cell 10. The sampling chute or diverter 22 is conventionally arranged for collecting the material 14 to be tested from a plurality of points across the conveyor belt 16 to provide a representative sampling of the material 14 thereon.

A material carrying member comprising a substantially funnel-shaped restricter cone 32 is suspended from an outlet port 33 of the test cell 10, for controlling the rate of flow of material 14 therethrough. The restricter cone 32 restricts the flow to a substantially even and constant rate, while keeping the test cell 10 substantially evenly filled with the material 14 flowing therethrough. Consequently, the material 14 is propelled through the test cell 10 by the force of gravity, in this embodiment.

In accordance with another embodiment of the invention, FIG. 2 illustrates a moisture tester 12b most beneficial for moisture measurement of low density, fine ground materials 14b such as hominy feed, fish meal, cotton seed meal, prepelletized formula feed and the like.

In the moisture tester 12b of FIG. 2, the test cell 10 of the present invention is connected to receive the material 14b at its inlet port 30 from the conveyor 16, via a funnel-like chute 22, substantially the same as the conveyor 16 and chute 22 of FIG. 1. Advantageously, the outlet port 33 of the test cell 10 is connected with a screw auger 44, which carries the material 14b away from the bottom of the test cell 10, to be returned to the hopper 18. The screw auger 44 is sized and driven at a speed such that the rate of flow of the material 14b through the test cell 10 is substantially constant and even, while maintaining the test cell 10 substantially evenly filled with the materials 14b to be tested.

Referring to FIG. 3, still another embodiment of a moisture tester, 12c, is illustrated. The moisture tester 12c includes a test cell 10, substantially identical to the test cell 10 of the embodiments of FIGS. 1 and 2. The embodiment of FIG. 3 is beneficial for use in measuring the moisture content of fibrous materials 14c such as chopped alfalfa or bermuda grass. A sample of the material 14c to be tested is delivered to the moisture tester 12c via a conveyor 16, and a hopper 18 is positioned to collect material from the conveyor 16 and the moisture tester 12c, in the same fashion as described above in the embodiments of FIG. 1 and FIG. 2. An inlet chute 46, similar to the chute 22 of FIGS. 1 and 2, is positioned adjacent the conveyor 16 for collecting a sample of material therefrom to be tested. Preferably, the chute 46 is somewhat larger at its inlet than the chute 22 for accomodating the relatively bulkier material 14c. An outlet 48 of the chute 44 is advantageously connected with a screw-type auger 50 similar to the auger 44 of FIG. 2, which feeds the inlet port 30 of the test cell 10, forcing the material 14c through the test cell, to be tested therein. An outlet tube 52 engages the outlet port 33 of the test cell 10, including a hinged door or cover member 54. Advantageously, the door 54 is spring loaded or otherwise yieldably biased against the open end of the outlet tube 52. In consequence of the cooperating action of the screw auger 50 and the yieldably biased, hinged outlet door 54, a substantially even and constant flow of material 14c is maintained through the test cell 10, the test cell 10 being substantially evenly filled with the material 14c to be tested.

It will further be noted that in FIGS. 1 through 3, a box-like structure 56, comprising an enclosure for a circuit portion of the moisture tester, is mounted on a side of the test cell 10. The circuit is described more fully hereinbelow.

Referring now to FIGS. 4 through 7 the test cell 10, constructed in accordance with the principles of this invention, is shown in additional detail. The test cell 10 includes a first electrode member 60 which comprises a generally cylindrical tube of electrically conductive material. It will be noted that the cylindrical tube 60 is open at both ends thereof, defining the inlet port 30, and the outlet port 33 for accomodating the flow of material therethrough. The cylindrical tube 60 includes a pair of radially outwardly extending flanges or flares 66 and 68, generally surrounding the respective inlet and outlet ports 30 and 33. The flanges 66 and 68 are provided with a number of apertures 70 for receiving suitable fasteners to hold the test cell 10 in place with respect to the other elements of the moisture tester, as illustrated in FIGS. 1 through 3. A second electrode member 72 comprises a generally planar body or plate of electrically conductive material disposed inside of the cylindrical tube 60. A support member 74 of electrical insulating material holds the second electrode member 72 closely adjacent a segment 61 of the inner wall of the cylindrical tube 60 and electrically isolated therefrom. The member 74 includes a section or portion 76 extending between the planar electrode 72 and the adjacent inner wall segment 61 of the cylindrical tube 60, and sloping towards the segment 61, in the direction of the inlet port 30. In the embodiment shown, the support member 74 is formed so that the electrode 72 is encapsulated thereby.

In accordance with a feature of the invention, the electrodes 72 and 60 form a capacitive type test cell defining a completely enclosed but unobstructed passageway 78 therebetween for accomodating the flow of material therethrough. In the embodiment shown in passageway 78 has a cross-sectional configuration which is continuous or uninterrupted. In other words, the passageway is not annular as is the case with certain heretofore suggested structures. The section or portion 76 of the support member 74 serves to direct the flow of material from the inlet port 30 towards the unobstructed passageway 78, which comprises the major portion of the interior volume of the tube 60. The section 76 also includes a suitable mounting aperture 77 formed therein for receiving a thermistor 92, which will be discussed more fully hereinbelow. It will be noted that the support member 74 has a lower flange portion 80, extending radially outwardly of the axis of the cylindrical tube 60 to abut the inner wall segment 61 thereof. Consequently, the support member 74, including the portions 76 and 80 thereof separate the relatively small volume in the tube 60, generally between the electrode 72 and adjacent wall segment 61, from the unobstructed passageway 78.

The support member 74, with the electrode 72 mounted therein, is secured to the adjacent wall segment 61 of the cylindrical tube 60 by suitable brackets 82, 84 and 86 of electrically nonconductive or insulating material. The brackets 82, 84, 86 comprising generally tubular members formed with internal and external threads. Screws 88 are provided securing the suppport member 74 to the brackets by engaging the internal threads of the brackets 82, 84, 86. The heads of the screws 88 are then preferably secured to the electrode 72, by welding, soldering, or the like, thus aiding in holding the electrode 72 in place. As best seen on bracket 82, in FIG. 5, the tubular bracket members 82, 84 and 86 have their threaded outer wall portions extended through complimentary openings in the side wall segment 61 of the cylindrical tube 60. Suitable fasteners such as nuts 90 engage these threaded portions for securing the brackets to the wall segment 61, thus drawing the support member 74, carrying the electrode 72, thereagainst. It will be noted that the tubular bracket members 84 and 86 are each provided with a small side opening or aperture for receiving a wire conductor. A wire conductor 94, extending through the tubular bracket 84, is conductively connected with the thermistor 92, and similarly, a wire conductor 96, extending through the tubular bracket 86, is conductively connected with the electrode member 72. The electrode member comprising the cylindrical tube 60 is in conductive connection with electrical ground.

The enclosure 56 is connected with the side wall segment 61 of the cylindrical tube 60 by a generally U-shaped bracket 98. It will be noted that the tubular brackets 84 and 86 extend through openings provided therefor in the bracket 98 and in the back wall of the enclosure 56, and the wires 94 and 96 extend therethrough to make contact with suitable portions of the circuits therein which are mounted on a circuit board 100 housed within the enclosure 56. The enclosure 56 is also provided with an outlet conduit 102 which carries a conductor cable 104 for providing a suitable signal from the moisture tester to appropriate readout or display panels, printers, or the like (not shown), for providing a suitable display of the moisture measurements.

Referring now to FIG. 7, a second embodiment of a test cell 10a is illustrated. The test cell 10a is substantially similar to the test cell 10 of FIGS. 5 and 6, however, the cylindrical tube 60a thereof is substantially shorter axially than the cylindrical tube 60 of FIG. 5. Thus, a support member 74a and second electrode member 72a mounted therein are of correspondingly shorter length than the electrode 72 and member 74 of FIG. 5. Also, in the embodiment of FIG. 7, it will be noted that only two tubular brackets, 84a and 86a, are required to suitably position the member 74 within the cylindrical tube electrode member 60a. In all other respects, the structure and function of the test cell 10a is substantially identical to the that of the test cell 10 of FIG. 6.

Figure 8B:
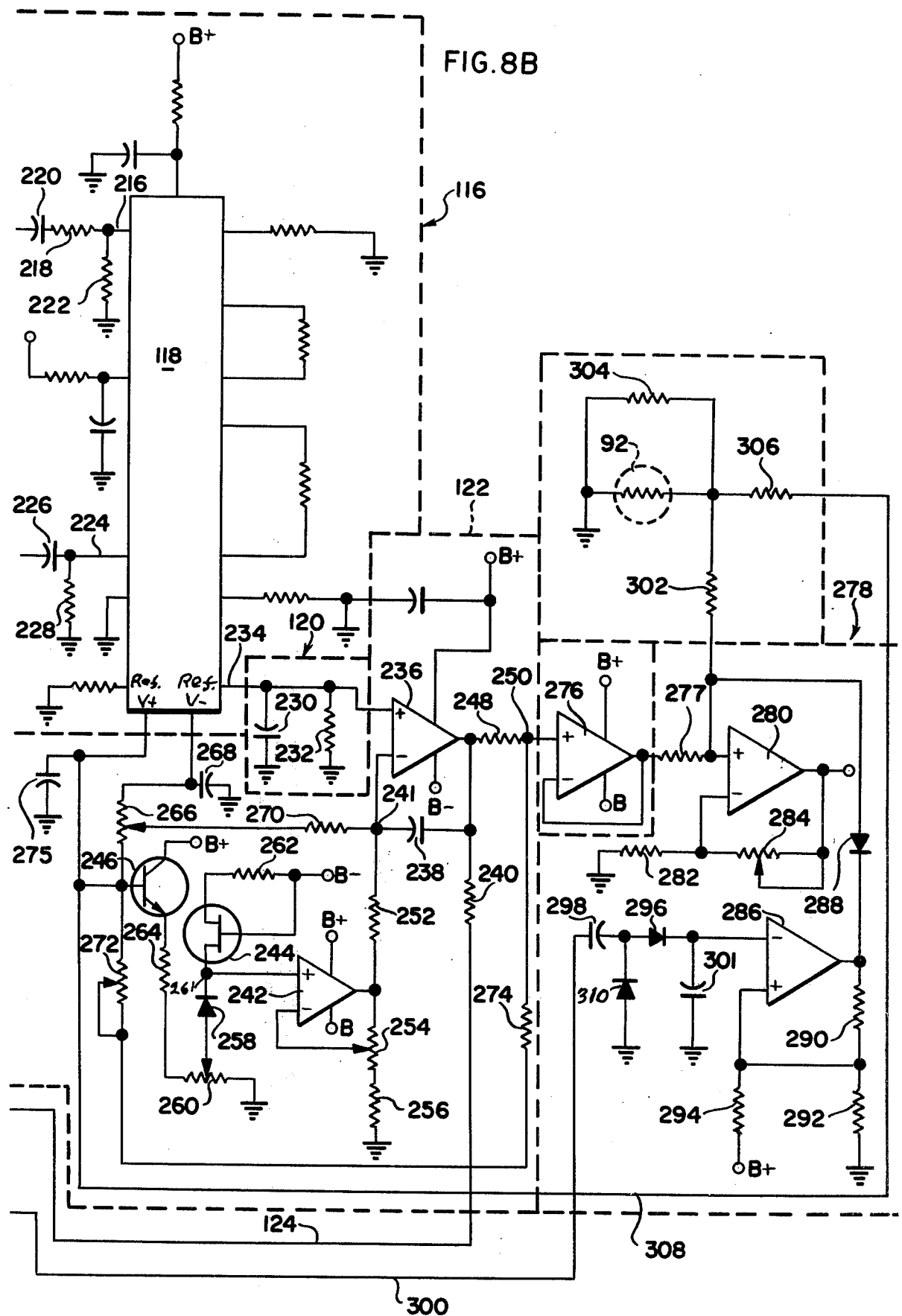

Referring now to FIG. 8, a circuit incorporated in the moisture tester of this invention is shown schematically. To facilitate clarity, the circuit is divided into FIGS. 8A and 8B, the lines at the left hand edge of FIG. 8B being continuations of corresponding lines at the right hand edge of FIG. 8A. The circuit of FIG. 8 is preferably mounted on the circuit board 100 within the enclosure 56, illustrated in FIGS. 5 and 7. To facilitate an understanding of the operation thereof, the circuit of FIG. 8 will be first described with reference to functional units or blocks thereof, as indicated by dashed lines.

An alternating current (AC) signal source 106, such as a crystal controlled oscillator, has an output at a terminal 108. The output signal at the terminal 108 is delivered to inputs of a fixed phase circuit 110, and to a capacitive impedance or test circuit 112, including the capacitive test cell 10, respectively. The capacitive impedance circuit 112 is connected with an input of a controlled phase shift circuit 114. The outputs of the fixed phase shift circuit 110 and of the controlled phase shift circuit 114 are delivered to a pair of inputs of a phase detector circuit 116 which comprises multiplier integrated circuit 118. The output of the phase detector circuit 116, comprising an output of the multiplier 118 thereof, is delivered to a low pass filter circuit 120, whose output is in turn delivered to an input of a DC amplifier circuit 122. The output of the DC amplifier circuit 122 is connected by a line 124 to an input 126 of the controlled phase shift circuit 114.

While it is not desired to be limited to a particular theory, the following is a theory which is believed to correctly exemplify the operation of the circuit components thus far described.

The output signal $E_s$ of the alternating signal source or oscillator 106, at the terminal 108 is characterized by the expression $E \sin \omega t$. The capacitive impedance circuit 112 including the test cell 10, and the controlled phase shift circuit 126 then operate on this signal, to give an output signal of the form $E_2 \sin(\omega t + \theta)$. Similarly, the fixed phase shift circuit 110 operates on the same input signal to give an output signal of the form $E_3 \sin(\omega t + \beta)$. The multiplier 118 of the phase detector circuit 116, then multiplies these two signals, to produce an output signal $E_2E_3 \sin(\omega t+\theta) \sin(\omega t+\beta)$, which by trigonometric identity may be expressed as:

$$\tfrac{1}{2}E_2E_3[\cos(\theta-\beta) - \cos(2\omega t+\theta+\beta)]$$

The low pass filter 120 substantially eliminates the second term of the foregoing expression, while the remaining DC term is passed on to the DC amplifier circuit 122. An output of the DC amplifier circuit 122 is then fed back on the line 124 to an input of the controlled phase shift circuit 126. This feedback signal is adjusted, as will be more fully described hereinbelow, such that the controlled phase shift circuit 114 provides a phase shift angle substantially 90° out of phase with the phase shift angle of the fixed phase shift circuit 110.

Referring now in detail to the capacitive impedance circuit 112, the terminal 108 is connected via the series combination of a resistor 128 and a capacitor 130 to an input terminal 132 thereof. The capacitive test cell 10 is connected between the terminal 132 and ground. A resistor 133 is connected to parallel with the capacitive test cell 10. The terminal 132 is connected via a capacitor 134 to the gate input of a FET 136, which terminal is also connected via a resistor 138 to a positive voltage supply and via a resistor 140 to ground. The drain terminal of the FET 136 is connected to a positive voltage supply and the source terminal thereof is connected to an input of the controlled phase shift circuit 114, and via a resistor 142 to ground. The controlled phase shift circuit 114 included a varicap diode 144, whose anode is connected to the input 126 on the line 124 from the DC amplifier circuit 122, and via a capacitor 146 to ground. The cathode of the varicap diode 144 is connected via a capacitor 148 in series with a resistor 150 to the output of the capacitive impedance circuit 112. The cathode of the varicap diode 144 is also connected via a resistor 152 to the junction of a series connected pair of resistors 154 and 156 which form a voltage divider between a positive voltage supply and ground. The junction of the capacitor 148 with the resistor 150 is connected to the gate input of a FET 158, which input is also connected by a resistor 160 to ground. The source input of the FET 158 is connected via a resistor 162 to ground, and the drain input thereof is connected to an input of the phase detector circuit 116, and via a resistor 164 to a positive voltage supply.

Continuing, with the theory of operation, it will be appreciated that the test cell capacitor 10 presents both a capacitance and a conductance factor which vary in accordance with the properties of the material therein to be tested. In the following discussion, the terms C1 and G1 are used to represent the active capacitance and conductance of the test cell 10, filled with the material to be measured, and C2 and G2 are used to express the net fixed, stray capacitance and conductance, respectively, the remaining portion of the circuit 112, excluding capacitor of 130. Similarly, C130, C146, C148, and R150 are used to represent the capacitance and resistance, respectively, of the like numbered elements. The output Ec of the capacitive impedance circuit 112 may be expressed as $E_1 \sin(wt+\delta)$. In complex variable notation, this signal may be expressed as:

$$Ec = \frac{E_s\,C130}{C_1 + C_2 + C130\,j(C'_1 + C'_2)}, \text{ where } C_n = \frac{G_n}{\omega}$$

This signal is then phase shifted by the network including the resistor 150 and the varicap diode 144. C146 and C148 are very large compared to the capacitance of the varicap 144, (C144), whereby their impedance may be neglected. Therefore, the output of the controlled phase shift circuit 114 at the input of the phase detector circuit 116, may be expressed as:

$$\frac{E_s\,C130}{C_1 + C_2 + C130 - j(C'_1 + C'_2)} \cdot \frac{1 - j\omega R150\,C144}{1 + R150^2 C144^2 \omega^2}$$

This expression may be set equal to the complex term $(a - jb)$ which corresponds to the resulting phase angle $\theta$ at the output of the controlled phase shift circuit 114. As described above, the phase detector circuit 116, low pass filter 120 and DC amplifier 122 provide a signal on the line 124 which is adjusted to cause a 90° phase angle between the two inputs of the phase detector circuit 116. Therefore, $(a-jb)$, corresponding to angle $\theta$ must also correspond to the angle $\beta-90°$ such that, $\tan^{-1} b/a = \theta = \beta - 90°$. With algebraic manipulation, the foregoing equation then becomes $$\omega R150\,C144 = b/a - \frac{\dfrac{C'_1 + C'_2}{C_1 + C_2 + C130}}{1 + b/a\,\dfrac{C'_1 + C'_2}{C_1 + C_2 + C130}}$$

and by trigonometric identity $$\omega R150\,C144 = \tan(\sigma + \theta), \text{ where } \tan\sigma = \frac{C'_1 + C'_2}{C_1 + C_2 + C130}$$

since C2, C2' and C130 are usually small as compared to C1 and C1', $$\tan\sigma \approx \frac{C1'}{C1}$$

which is the definition of the loss tangent of the material being measured.

The capacitance (C144) of the varicap diode 144 is a function of the voltage signal applied thereto on the line 126 and is of the form $$\frac{KC_o}{E^{\frac{1}{2}}}$$

therefore, the foregoing may be rewritten $$R150\,\frac{KC_o}{E^{\frac{1}{2}}} = \tan(\sigma + \theta)$$

$$E = (R150\,\omega K C_o)^2 \cot^2(\delta+\theta)$$

therefore, the signal on the line 124, which corresponds to the output of the DC amplifier circuit 122 is proportional to the term $\cot^2(\delta+\theta)$. It can be shown that the loss tangent of a material is essentially independent of the density of the material. Thus, the foregoing expression is directly proportional to the inverse square of the loss tangent, and is therefore also independent of density.

While the specific circuit illustrated in FIG. 8 is described in detail hereinbelow, it will be appreciated that the invention is not limited thereto. Those skilled in the art may devise alternate arrangements for achieving the operation described above, and such alternative arrangements form a part of this invention, insofar as they fall within the spirit and scope of the appended claims.

The alternating current signal source circuit 106 comprises a crystal controlled oscillator including a pair of NPN transistors 166 and 168, and a crystal element 170, which preferably comprises a 1 Mhz crystal element. One side of the crystal element 170 is connected with the base electrode of the transistor 166, and also to the junction of a pair of resistors 172, 174 which are connected as a voltage divider in series between a positive and negative voltage supply. A pair of capacitors 176 and 178 are connected between the respective positive and negative voltage supplies and ground. The opposite side of the crystal element 170 is connected with the collector electrode of the transistor 166 and also via an inductor 180 to the positive voltage supply. A pair of capacitors 182 and 184 are connected in series from the positive voltage supply to the collector electrode of the transistor 166, the junction of the capacitors 182 and 184 also being connected to the emitter electrode thereof, which electrode is also connected by a resistor 186 to the negative voltage supply. The emitter electrode of the transistor 166 is also connected via a capacitor 188 to the base electrode of the transistor 168, which electrode is also connected to the junction of a pair of resistors 190 and 192 which are connected in series between a positive and a negative voltage supply. The collector electrode of the transistor 168 is connected to the positive voltage supply and via a capacitor 194 to the negative voltage supply. The emitter electrode of the transistor 168 is connected to the terminal 108 at the input of the fixed phase shift circuit 110, and also via a resistor 196 to the negative voltage supply.

The fixed phase shift circuit 110 includes a FET 198 whose gate input is connected via the series combination of resistors 200, 202 and 204 to the terminal 108. A resistor 206 is connected in parallel with the resistor 200. A capacitor 208 is connected between the junction of the resistor 202 with the resistor 204 and ground. Similarly, a capacitor 210 is connected between the junction of the resistor 202 with the resistors 200 and 206 and ground. A capacitor 212 is connected between the gate input of the FET 198 and ground. The drain input of the FET 198 is connected to the positive voltage supply and the source terminal thereof is connected to an input of the phase detector circuit 116 and via a resistor 214 to the negative voltage supply.

The phase detector circuit 116 includes the multiplier integrated circuit 118 which in the illustrated embodiment comprises an integrated circuit of the type MC1594L. A first input 216 of the multiplier 118 is connected via the series combination of a resistor 218 and a capacitor 220 to the output of the fixed phase shift circuit 110, at the source terminal of the FET 198 thereof. The terminal 216 is also connected by a resistor 222 to ground. Similarly, a second input terminal 224 of the multiplier 118 is connected via a capacitor 226 to the output of the controlled phase shift circuit 114, which is the drain terminal of the FET 158 thereof. The terminal 224 is also connected via a resistor 228 to ground. The remaining terminals of the multiplier integrated circuit are connected with resistive and capacitive circuit elements in conventional fashion, and need not be described further herein.

The low pass filter 120 comprises the parallel combination of a capacitor 230 with a resistor 232 which is connected between an output 234 of the multiplier circuit 118 and ground.

The output terminal 234 is also connected to the input of the DC amplifier circuit 122 which comprises the noninverting input of an operational amplifier 236. The operational amplifier 236 may comprise an operational amplifier of the type designated generally 741, and includes conventional connections to a positive and negative voltage supply, respectively. The inverting input of the operational amplifier 236 is connected via a capacitor 238 to the output thereof, which output is also connected by a resistor 240 to the line 124 described above. The inverting input of the operational amplifier 236 is also connected at a terminal 241 to a portion of the DC amplifier circuit 122 including an operational amplifier 242, a FET 244 and a NPN transistor 246. The output of the operational amplifier 236 is connected via a resistor 248 to a terminal 250. The operational amplifier 242, in the illustrated embodiment, comprises one half of a dual op amp integrated circuit of the type 5558, and is provided with conventional connections to positive and negative voltage supplies. The output of the op amp 242 is connected via a resistor 252 to the terminal 241 and to one side of a potentiometer 254 whose opposite side is connected via a resistor 256 to ground and whose wiper arm is connected to the inverting input of the op amp 242. The noninverting input of the op amp 242 is connected to the drain terminal of the FET 244, which terminal is also connected to the cathode of a diode 258 whose anode is connected to the wiper arm of a potentiometer 260. The source terminal of the FET 244 is connected via a resistor 262 to the negative voltage supply, and the gate terminal is connected to the negative voltage supply. The potentiometer 260 has one end thereof connected to ground and the other end connected via a resistor 264 to the emitter electrode of the transistor 246, whose collector electrode is connected to the positive voltage supply. The base electrode of the transistor 246 is connected to one side of a potentiometer 266 whose opposite side is connected via a capacitor 268 to ground, and whose wiper arm is connected via a resistor 270 to the terminal 241. The base electrode of the transistor 246 is also connected to one side of a potentiometer 272 whose wiper arm and opposite side are connected together via a resistor 274 to the terminal 250. The base electrode of the transistor 246 is also connected via a capacitor 275 to ground. It will be appreciated that the foregoing circuit can be adjusted to provide the appropriate signal on the line 124 to the varicap diode 144, for setting the phase angle shift provided thereby, as described above. The setting of the potentiometer 266 achieves this purpose by providing an offset to the multiplier 118 output, thereby forcing a phase-shift between the two inputs 218 and 224 to compensate for the output.

The circuit portion comprising transistors 244, 246, op amp 242, and adjusting potentiometers 254, 260, along with associated resistors comprises a temperature compensation circuit for the multiplier 118. Diode 258 provides a temperature sensor and transistor 244 along with resistor 262 provides a current source. Transistor 246, resistor 264, and potentiometer 260 provide an adjustable voltage reference and op amp 242 and potentiometer 254 adjust the amount of temperature compensation. The putput of the circuit is an adjustable temperature dependent voltage which cancels the temperature dependent offset of the multiplier 118.

When adjusting the circuit, potentiometer 260 is adjusted at room temperature until the voltage at point 261 is zero. Temperature is then applied (either hot or cold) and the offset monitored. Potentiometer 254 is then adjusted to cancel the offset.

The remaining circuits illustrated in FIG. 8B provide a suitable output signal, corresponding to the moisture content of the material being tested. This signal may be used to drive external components such as read-out or print-out devices, for providing a continuous display and/or record of the moisture content of the material flowing through the test cell. A buffer circuit comprising an operational amplifier 276 is connected to receive the signal at the terminal 250, at the noninverting input thereof. The operational amplifier 276, in the illustrated embodiment, comprises one op amp of a two op amp package of the type 5558, and is provided with conventional connection to the positive and negative voltage supplies. The output of the op amp 276 is connected with the inverting input thereof, and via a resistor 277 to an adjustable gain amplifier circuit 278, which input comprises the noninverting input of an operational amplifier 280. In the illustrated embodiment, the op amp 280 comprises the second op amp of one of the dual op amp packages of the type 5558 described. The output of the op amp 280 comprises the output of the circuit for providing a signal to other elements, as described above. The inverting input of the op amp 280 is connected via a resistor 282 to ground, and to one side of a potentiometer 284 whose wiper arm and opposite side are connected together to the output of the op amp 280. An operational amplifier 286 has its output connected to the cathode of a diode 288, whose anode is connected with the noninverting input of the op amp 280. In the illustrated embodiment the op amp 286 comprises the second op amp of a dual op amp package 5558. The output of the op amp 286 is also connected via a series connected pair of resistors 290 and 292 to ground. The junction of the resistors 290 and 292 is connected with the noninverting input of the op amp 286, which input is also connected via a resistor 294 to the positive voltage supply. The inverting input of the op amp 286 is connected to the cathode of a diode 296 whose anode is connected to the cathode of diode 310 having an anode connected to ground. The anode of diode 296 is also connected via a capacitor 298 to a line 300, the line 300 being connected in FIG. 8A to the source terminal of the FET 136. The inverting input of the op amp 286 is also connected via a capacitor 301 to ground.

Op amp 286 and its associated circuitry comprise an empty cell detection circuit. Diodes 296, 310 are a peak detecting circuit and capacitor 301 charges to the peak positive voltage seen by diode 296 and 310. If the voltage at the inverting input of op amp 286 is more positive than the reference voltage on the noninverting input, op amp 286 is in negative saturation. The reference voltage is set by resistors 292, 294 and the voltage level of B+. Amplifier 286 has positive feedback through resistor 290, thereby creating a "snap" action effect. Thus, if the peak voltage of the cell circuit exceeds the threshold at the noninverting input, op amp 286 "snap" into negative saturation pulling the noninverting input and the output of 280 negative.

The thermistor 92, as described above, is mounted in the test cell 10 to be in thermal contact with the material flowing therethrough, and has one end thereof connected to ground and the other end thereof connected via a resistor 302 to the noninverting input of the op amp 280. A resistor 304 is connected in parallel with the thermister 92. The junction of the resistor 304 with the resistor 302 is connected via a resistor 306 to a line 308, which line is connected via the capacitor 275, described above, to ground. Thus, the output of the adjustable gain amplifier 278 is temperature corrected, in accordance with the variations in temperature of the material being tested in a test cell 10.

While specific embodiments have been shown and described herein, the invention is not limited thereto. Such changes and modifications as may occur to those skilled in the art also constitute a part of the invention, insofar as they fall within the spirit and scope of the appended claims.

The invention is claimed as follows:

1. A moisture tester for continuously measuring the moisture content of a material flowing therethrough, comprising: a first electrode member comprising a generally cylindrical tube of electrically conductive material, a second electrode member comprising a generally planar body of electrically conductive material disposed inside of said first electrode member closely adjacent an inner wall thereof and electrically isolated therefrom, said electrodes defining a capacitive test cell having a substantially unobstructed passageway between the electrodes, said tester further including material carrying means connected with said passageway for providing a substantially even flow of material therethrough and for cooperating with said passageway to maintain said passageway substantially evenly filled with said flowing material, and circuit means electrically connected with said capacitive test cell for producing signal means corresponding to the moisture content of said material flowing therethrough, in accordance with electrical properties of the material-filled capacitive test cell.

2. A moisture tester according to claim 1 wherein said cylindrical tube comprising said first electrode includes a top inlet port and a bottom outlet port, respectively, and said second electrode member further includes a section extending between said planar body and said closely adjacent inner wall and sloping toward said inlet port, for directing said material to be tested from said inlet port through said unobstructed passageway.

3. A moisture tester according to claim 2 wherein said material carrying means includes chute means positioned adjacent said inlet port for delivering a supply of material thereto, and screw auger means connected with said outlet port for carrying said material away therefrom at a predetermined rate for adapting said moisture tester for moisture measurement of low density, fine ground materials.

4. A moisture tester according to claim 2 wherein said material carrying means include chute means connected with said inlet port for delivering a supply of material to be tested thereto and restricter cone means connected with said outlet port for restricting the flow of material therethrough to a predetermined rate, adapting said tester for moisture measurement of readily flowing granular material.

5. A moisture tester according to claim 2 wherein said material carrying means includes screw auger means connected with said inlet port for providing material thereto at a predetermined rate and a closure member attached to said outlet port and including means yieldably biasing said closure member thereagainst, for maintaining said test cell substantially filled at said predetermined flow rate of said screw auger means, adapting said tester for moisture measurement of fibrous material.

6. A moisture tester according to claim 1 wherein said circuit means includes means for producing said signal means corresponding to the moisture content of said material substantially independent of the density of said material and of variations therein.

7. A continuous flow moisture tester comprising: a first electrode member of electrically conductive material, a second electrode member of electrically conductive material disposed in a predetermined orientation with respect to said first electrode member for defining a substantially unobstructed, open-ended passageway enclosed by said first and second electrode members, said first and second electrode members being electrically isolated to form a capacitive test cell, material carrying means connected with said test cell for providing a substantially even flow of material therethrough and for maintaining said test cell substantially filled with said flowing material, and circuit means connected with said capacitive test cell for providing signal means corresponding to the moisture content of said material flowing therethrough substantially independent of the density thereof or variations in said density and in accordance with the electrical properties of said material-filled capacitive test cell and wherein said circuit means includes oscillator means, fixed phase shift means connected with said oscillator means, controlled phase shift means, said capacitive test cell being electrically connected in a test network connected between said oscillator means and said controlled phase shift means, phase detector means connected to said fixed and to said controlled phase shifting means and amplifier means connected with said phase detector means, an output of said amplifier means being connected with said controlled phase shift means for maintaining the phase shift provided thereby at a substantially 90° phase angle difference with the phase shift provided by said fixed phase shift means for producing an output signal from said amplifier means substantially proportional to the loss tangent of the material being tested.

8. In a continuous flow moisture tester, the combination comprising: a first electrode member comprising an open-ended tube of electrically conductive material, a second electrode member comprising a sheet of electrically conductive material disposed inside of said first electrode member for defining therewith a capacitive test cell, and means holding said second electrode member closely adjacent to and at least partially abutting an inner wall segment of said tube and electrically isolated therefrom to define a single substantially unobstructed passageway between the second electrode and the remainder of the inner wall of the tube, said passageway comprising a major portion of the interior volume of said tube for the unobstructed flow of material therethrough, said tester further including material carrying means connected with said passageway for providing a substantially even flow of material therethrough and for cooperating with said passageway to maintain said passageway substantially evenly filled with said flowing material, and circuit means electrically connected with said capacitive test cell for producing signal means corresponding to the moisure content of said material flowing therethrough, in accordance with electrical properties of the material-filled capacitive test cell.

* * * * *

UNITED STATES PATENT AND TRADEMARK OFFICE
CERTIFICATE OF CORRECTION

PATENT NO. : 4,168,466
DATED : September 18, 1979
INVENTOR(S) : Robert R. Boldt

It is certified that error appears in the above-identified patent and that said Letters Patent are hereby corrected as shown below:

Column 6, line 40, after "phase" insert --shift--.

Signed and Sealed this

Twenty-ninth Day of January 1980

[SEAL]

Attest:

SIDNEY A. DIAMOND

Attesting Officer

Commissioner of Patents and Trademarks